(12) United States Patent
Suzuki et al.

(10) Patent No.: US 6,464,685 B1
(45) Date of Patent: Oct. 15, 2002

(54) ENDOSCOPIC LIGATION KIT

(75) Inventors: Zenetsu Suzuki; Haruhiko Masuda, both of Akita (JP)

(73) Assignee: Sumitomo Bakelite Company LTD, Tokyo (JP)

( * ) Notice: Subject to any disclaimer, the term of this patent is extended or adjusted under 35 U.S.C. 154(b) by 83 days.

(21) Appl. No.: 09/656,733

(22) Filed: Sep. 7, 2000

Related U.S. Application Data

(63) Continuation-in-part of application No. 09/125,524, filed as application No. PCT/JP97/00930 on Mar. 21, 1997.

(30) Foreign Application Priority Data

Dec. 27, 1996 (JP) .............................. 8-349171

(51) Int. Cl.[7] .................. A61M 25/16; A61B 17/10; A61B 1/00
(52) U.S. Cl. .................. 604/534; 606/140; 600/104
(58) Field of Search ................... 604/523, 533–535, 604/537; 606/139–141, 144, 148; 600/104, 127, 106

(56) References Cited

U.S. PATENT DOCUMENTS

| 4,226,239 A | 10/1980 | Polk et al. |
| 5,269,789 A | 12/1993 | Chin et al. |
| 5,507,797 A | * 4/1996 | Suzuki et al. ............... 606/139 |
| 5,569,268 A | 10/1996 | Hosoda |
| 5,788,715 A | * 8/1998 | Watson et al. ............... 606/140 |
| 6,136,009 A | * 10/2000 | Mears ......................... 606/140 |

FOREIGN PATENT DOCUMENTS

| JP | 53-38185 | 4/1978 |
| JP | 7-255733 | 10/1985 |
| JP | 7-59786 | 3/1995 |
| JP | 8-10217 | 1/1996 |

* cited by examiner

Primary Examiner—Michael J. Hayes
(74) Attorney, Agent, or Firm—Smith, Gambrell & Russell

(57) ABSTRACT

An endoscopic ligation kit including an inner cylinder, an outer cylinder having at least two step portions of diminishing outer radii formed on the outer periphery of its distal end portion, and a slide cylinder provided between the inner cylinder and the outer cylinder. The outer cylinder has a notch extending from its distal end portion to its maximum outer diameter portion. The slide cylinder has at its distal end portion a projection which conforms in size to the notch, and has steps and the projection is fitted in the notch. O-rings are mounted respectively on the outer periphery of the distal end portion of the inner cylinder and the step portions of the outer cylinder.

10 Claims, 6 Drawing Sheets

ENDOSCOPIC LIGATION KIT

REFERENCE TO A RELATED APPLICATION

This is a Continuation in Part application based on the U.S. patent application Ser. No. 09/125,524, filed on Dec. 11, 1998, now abandoned and incorporated herein. Ser. No. 07/125,524 is based on PCT/JP97/00930 filed Mar. 21, 1997.

INTRODUCTION AND BACKGROUND

This invention relates to one of the treatment methods for gastric and esophageal varices resulting from a liver disease. The invention relates to an endoscopic ligation kit used in a ligation operation in which a varix is ligated to thereby mechanically shut off a blood circulation so as to reduce, extinguish or thrombose the varix.

A mainstream treatment for gastric and esophageal varices due to liver cirrhosis or the like has heretofore been an endoscopic injection Sclerotherapy (EIS) in which an indurating agent, having a blood-coagulating nature, is injected into the varix or a portion outside the varix, and thus effecting treatment.

However, the perivenous administration of the medicine, having side effects on the living body, has caused various complications, such as a pulmonary embolism, and pulmonary failure and kidney disorder, in combination with complicated blood circulation kinetics of a portal hypertension. Therefore, a dose of the indurating agent is limited, and the treatment is carried out, taking the recovery of the patient into consideration, and therefore there has been encountered a problem that the treatment time is prolonged.

Recently, an esophageal varices ligation (EVL) has been used as a treatment method for gastric and esophageal varices. As shown in FIG. 7, EVL is a technique in which a varix 14 is drawn into a tubular device 11 mounted on a distal end of an endoscope 6, and an O-ring 4, beforehand expanded and fitted on an outer periphery of a cylinder 12, is disengaged from this cylinder by pulling the cylinder 12 by means of a wire inserted through a biopsy channel, and is fitted on a proximal end portion of the varix 14 drawn into a polyp-like shape, and the varix is mechanically ligated by a contracting force of rubber of the O-ring, thereby devastating the varix.

A currently-used ligation kit will now be described with reference to the drawings. FIG. 6B shows the construction of a ligation kit now extensively used, and tubular device 11, mounted on a distal end of an endoscope 6, comprising an endoscope mounting portion 7, an outer tube 3, and a cylinder 12 having an O-ring 4 mounted on a distal end portion thereof, a wire 13, passed through the biopsy channel 9 in the endoscope, is beforehand connected to the cylinder 12, and when the wire 13 is pulled, the cylinder 12 is retracted, so that the O-ring 4 is pushed by the outer tube, and is disengaged from the cylinder 12.

FIG. 6A shows a pneumatically-driven ligation kit having a principle difference from that of FIG. 6B. In this method, a slide cylinder 2 is provided between an inner cylinder 1 and an outer cylinder 3, and a fluid is fed under pressure from a syringe 10 via a connector 8 and a tract tube 5, and causes the slide cylinder 2 to be projected so as to disengage the O-ring 4, thereby ligating a varix. In the EVL using such an endoscopic ligation kit, it is not necessary to use a large amount of an induration agent as in the conventional EIS, and this is a highly-safe treatment method having little side effects on the patient, and besides any particularly difficult technique is not required when effecting the treatment, and the ligating treatment can be carried out safely with a simple operation, and therefore the number of facilities, adopting this treatment method, has been abruptly increasing.

However, in either of the devices, the endoscope must be withdrawn each time one ligation is effected, and then another O-ring must be set in position, and therefore much time has been required for inserting and withdrawing the endoscope.

A guide tube is kept in the pharynx so as to facilitate the insertion and withdrawal of the endoscope, and when withdrawing the endoscope after the ligation, the device, mounted on the distal end of the endoscope, is, in some cases, caught by a distal end of the guide tube, and is disengaged from the endoscope. In this case, the device, remaining in the body, is withdrawn by inserting a withdrawing forceps through the biopsy channel in the endoscope, and during this time, the treatment is interrupted. Furthermore, when inserting the guide tube, the mucosa is, in some cases, may be damaged by the distal end of the guide tube. As a result, a type of device which is capable of successively effecting ligations and does not use a guide tube, has been desired in the market.

SUMMARY OF THE INVENTION

In order to overcome the problem of the conventional endoscopic ligation kits that the endoscope must be withdrawn each time one ligation is effected, and before another O-ring can be attached, the present invention has been studied in various ways, and an object thereof is to provide an endoscopic ligation kit which is capable of successively effecting ligations safely and positively.

There is provided an endoscopic ligation kit for attachment to a distal end of an endoscope so as to draw and ligate a tissue in a body cavity, such as gastric and esophageal varices, characterized in that the kit comprises an inner cylinder which has a rib at an outer periphery of its rear end portion, an outer cylinder which has at least two steps of diminishing outer radii formed on an outer periphery of its distal end portion and has at least one notch extending from its distal end to its maximum outer diameter portion, and a slide cylinder which has at least one projection at its distal end portion and has a seal ring fixedly secured to its rear end portion, the projection conforms in size to the notch in the outer cylinder and has steps, the slide cylinder is received in the bore of the outer cylinder in such a manner that the projection of the slide cylinder is fitted in the notch in the outer cylinder, the inner cylinder is inserted into a bore of the slide cylinder, so that the outer cylinder and the inner cylinder are integrally connected together through the rib of the inner cylinder, this assembly is mounted on a distal end of a mounting tube and O-rings are mounted respectively on the outer periphery of the distal end portion of the inner cylinder and the step portions of the outer cylinder, an annular hermetic space is formed at a rear side of the seal ring by the seal ring, fixedly secured to the rare end of the slide cylinder, the outer cylinder and the inner cylinder, and the projection, formed on the slide cylinder, is projected forwardly by a fluid, inserted through a tube connected to a small hole in a rear end of the annular hermetic space, and disengages the O-ring, mounted on the outer periphery of the distal end portion of the inner cylinder, therefrom, and also moves the O-rings, mounted respectively on the step portions of the outer cylinder, to the forwardly-adjacent step portions, respectively.

In the above endoscopic ligation kit, a spring is provided on a distal end side of a space in which the slide cylinder can slide, and the slide cylinder, after being projected, is returned by the spring.

DETAILED DESCRIPTION OF THE INVENTION

Figure 1A:
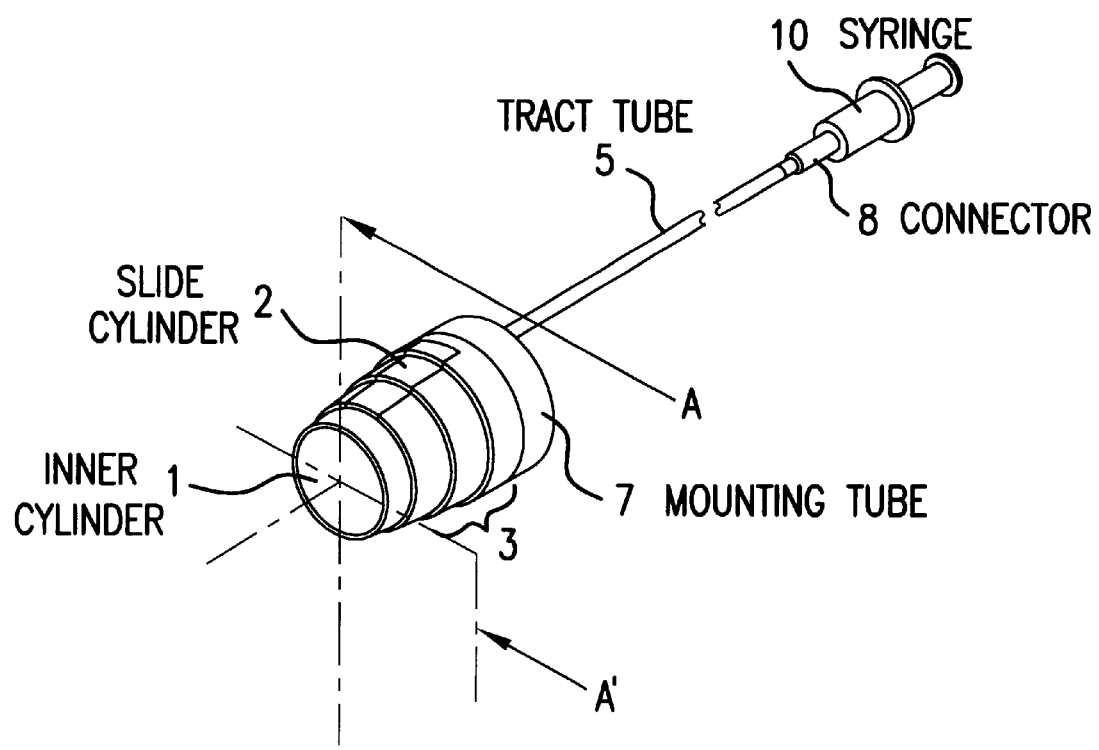
FIG. 1A is a perspective view of a ligation kit used in the present invention, which view shows a distal portion of the inner ring, a projection of the slide cylinder in the notch of the outer cylinder and the outer cylinder where no O-rings are mounted.
Figure 1B:
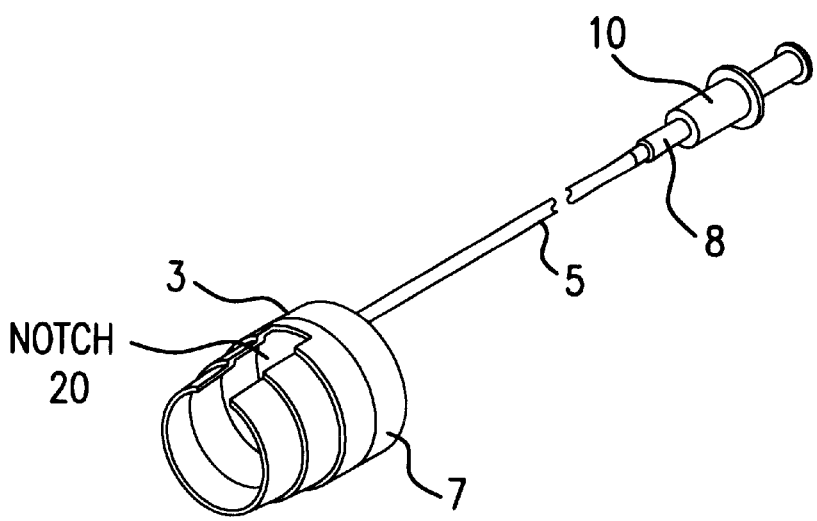
FIG. 1B is a perspective view of a ligation kit used in the present invention, which view shows an outer ring and an unfilled notch in the outer ring.
Figure 2A:
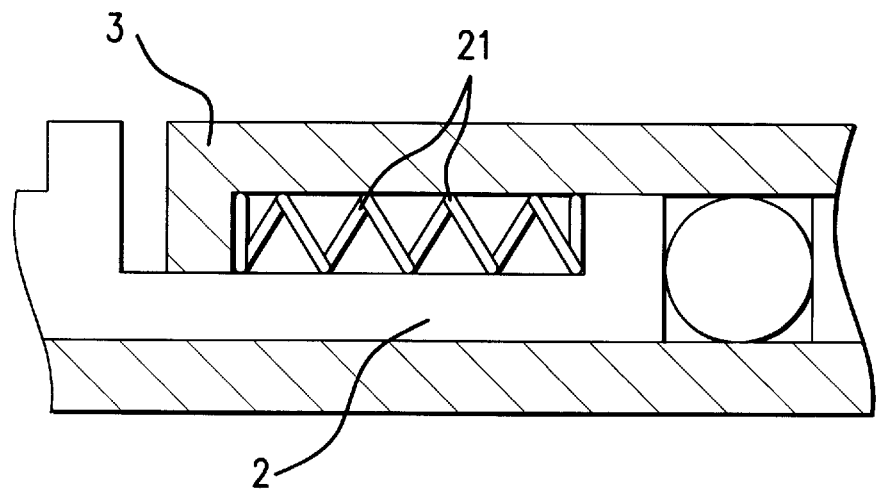
FIG. 2A is an enlarged view of the portion of FIG. 2B which shows an arrangement of a spring between an outer cylinder and a slide cylinder in proximity to a sealing ring.

The present invention will now be described in detail with reference to the drawings. FIGS. 1A, 1B, 2A and 2B are views showing one embodiment of a ligation kit of the present invention. FIG. 1A is a perspective view showing a condition in which O-rings are not mounted. FIG. 1B shows FIG. 1A with the outer cylinder 3 and slide cylinder 2 removed. FIG. 2A shows an enlarged view of the spring return mechanism of FIG. 2B. 2B is a cross-sectional view taken along the line A–A' of FIG. 1A, showing a condition in which the kit is attached to an endoscope. As shown in FIG. 3, the ligation kit of the present invention comprises an inner cylinder 1 which forms a hood for drawing a varix by suction, and has a rib 16 at its rear end, an outer cylinder 3 which has at least two step portions 17 of diminishing outer radii formed on its outer periphery, and has a notch extending from its distal end to its maximum outer diameter portion, and a slide cylinder 2 which has at its distal end portion a projection 18 (which conforms in size to the notch in the outer cylinder 3, and has steps 19), and has a sealing ring 15 fixedly secured to its rear end portion. As shown in FIG. 1A, the slide cylinder 2 is received in the outer cylinder 3 in such a manner that the projection of the slide cylinder 2 is fitted into the notch 20 in the outer cylinder 3, and the inner cylinder 1 is inserted into the bore of the slide cylinder, so that the outer cylinder 3 and the inner cylinder 1 are integrally connected together through the rib of the inner cylinder 1, and this assembly is fixed to a distal end of a mounting tube 7. Further, an air-tight annular space is formed at the rear side of the seal ring 15, between the seal ring, fixedly secured to the rear end of the slide cylinder 2, the outer cylinder 3 and the inner cylinder 1. A tract tube 5 for feeding a fluid is connected to a rear end of the annular space, and a syringe 10 is connected to a rear end of the tract tube 5, and a connector 8 for injecting the fluid is provided.

Figure 4:
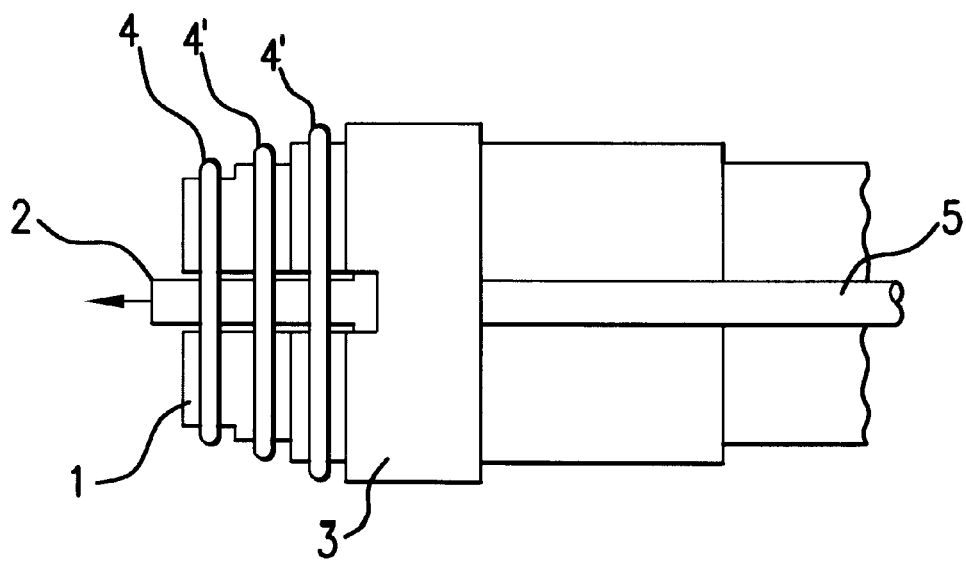
FIG. 4 is a plan view of the assembled kit including mounted O-rings.

An O-ring 4 is mounted on the outer periphery of the distal end portion of the inner cylinder 1, and also second and third O-rings 4' are mounted respectively on the step portions of the outer cylinder 3, and the fluid is fed through the tube 5 into the annular hermetic space to slide the slide cylinder 2 forwardly, so that the projection, formed on the slide cylinder, is projected forwardly, and disengages the O-ring 4, mounted on the outer periphery of the distal end portion of the inner cylinder 2, therefrom, and also moves the second and third O-rings 4', mounted respectively on the step portions 17 of the outer cylinder, to the forwardly-adjacent steps portions 17, respectively. Then, the fluid is drawn by the syringe 10, so that the slide cylinder 2 is returned to the condition it was in before it was projected, and the next ligation can be effected. It is suitable that in order to return the slide cylinder 2 to the condition before it is projected, a spring 21 is provided. A spring 21 may be provided in the annular hermetic space 22 between the slide cylinder 2 and the outer cylinder 3. FIG. 4 shows a plan view of the kit with the slide cylinder 2 being moved toward the distal end of the inner cylinder 1 to dispense the O-ring 4 and advance the O-rings 4'.

Figure 5:
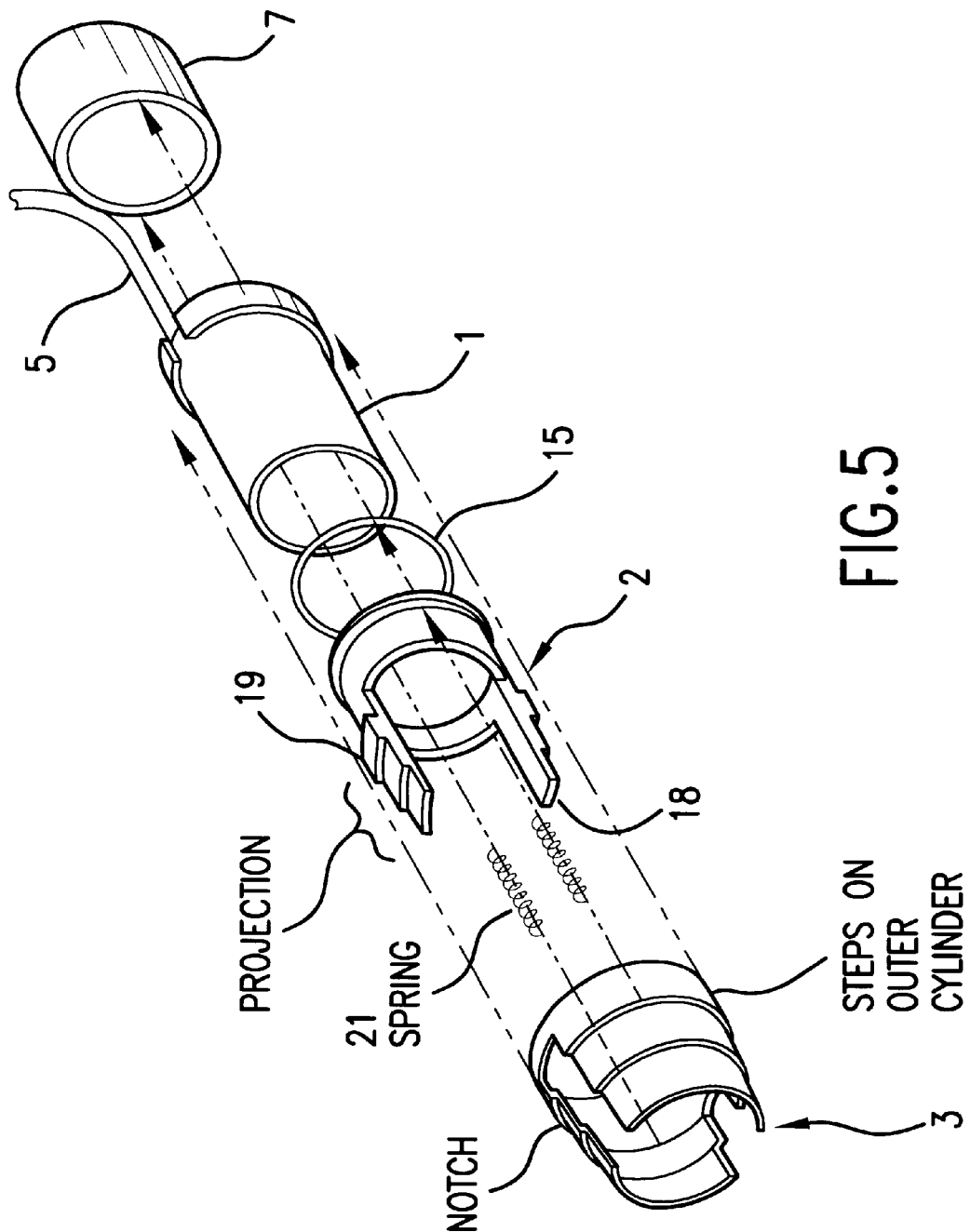
FIG. 5 is a perspective view of the disassembled parts of the kit.
Figure 6A:
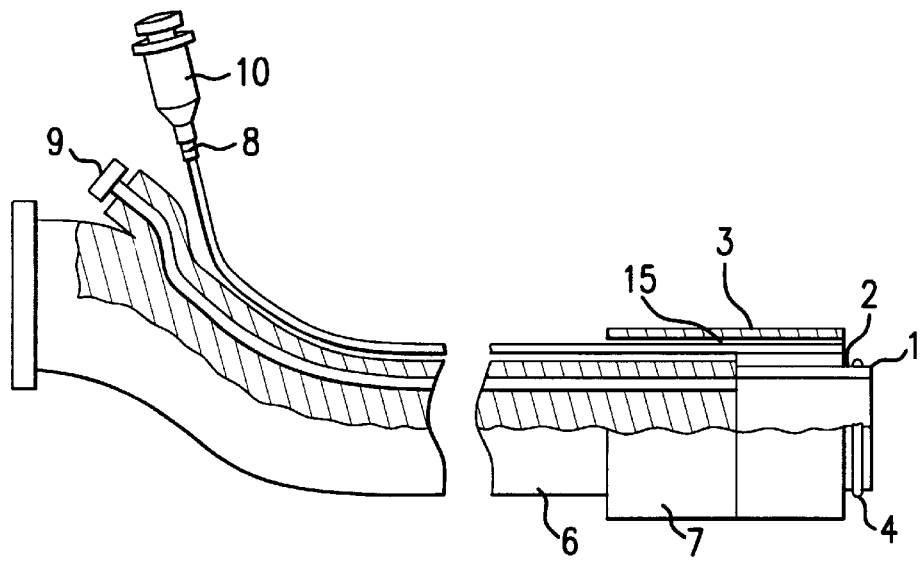
FIGS. 6A and 6B are views showing conventional endoscopic ligation kits, respectively.
Figure 6B:
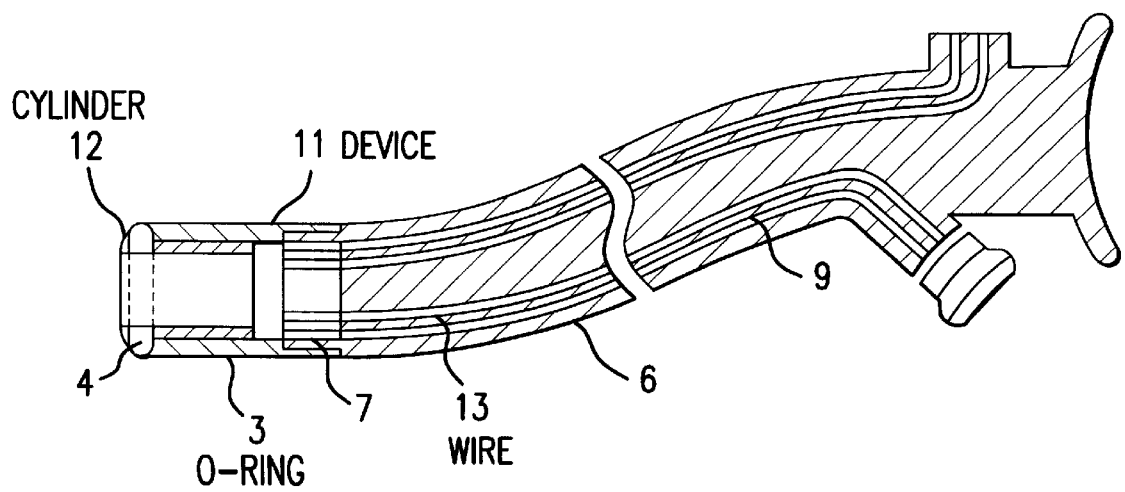
Figure 7:
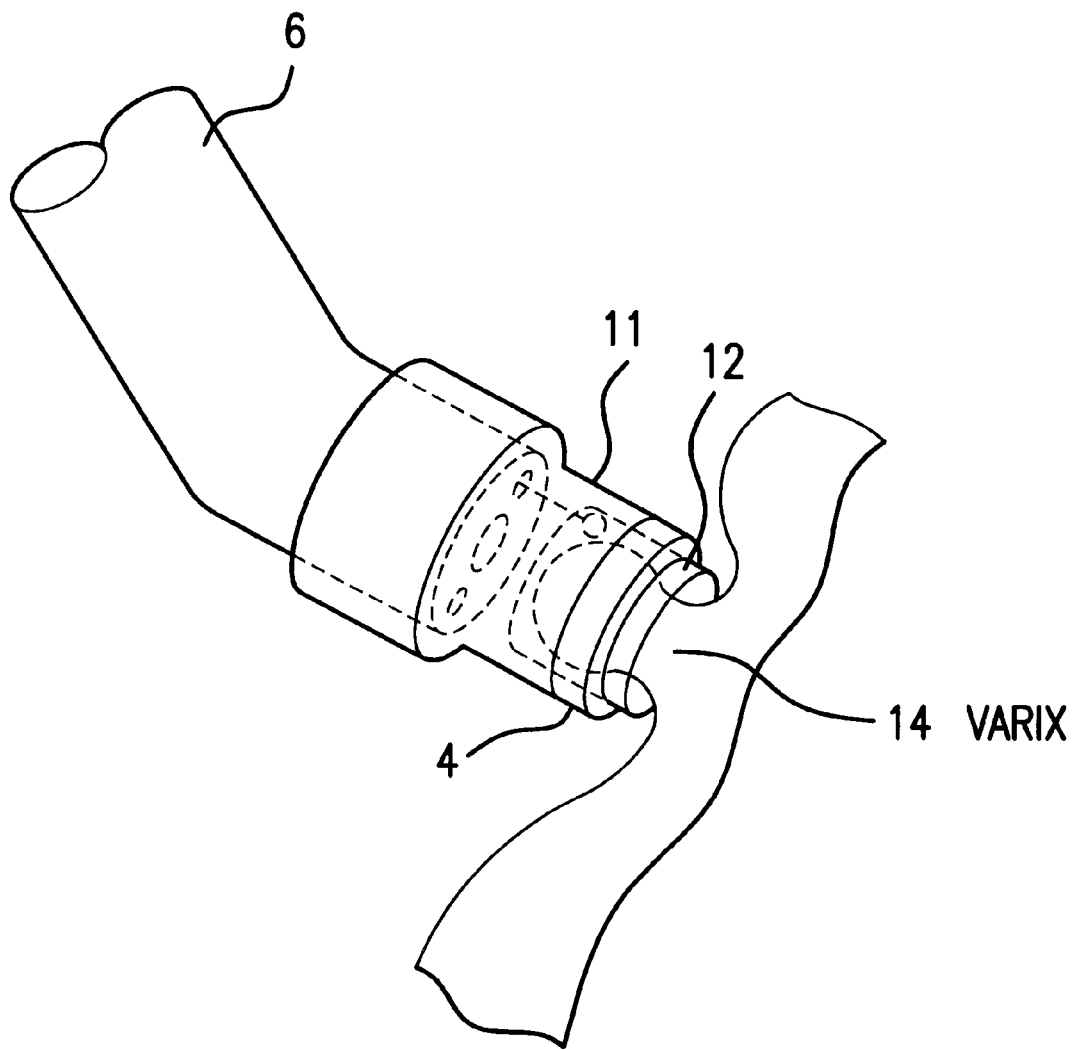
FIG. 7 is a view showing the manner of using an endoscopic ligation kit.

FIG. 5 shows a perspective view of the disassembled parts of the kit aligned so as to show how the order of assembly of the individual parts. As shown in FIG. 5, spring 21 is placed between the slide cylinder 2 and the outer cylinder 3 and the slide cylinder 2 is inserted into the bore of the outer cylinder 3 and the projection 18 of the slide cylinder 2 is also inserted into the notch 20 of the outer cylinder 3. The seal ring 15 is placed on the slide cylinder and fixed thereto. The inner cylinder 1 is then inserted into the bore of the slide cylinder 2 until the rib 16 of the inner cylinder 1 sealably contacts the rear end of the outer cylinder 3.

That portion of the rear end of the slide cylinder 2 (fitted in the notch portion in the outer cylinder), to which the seal ring 15 is fixedly secured, has a ring-like. shape, and the slide cylinder has at its distal end portion the projection which conforms in size to the notch 20 in the outer cylinder 3, and has the steps 19, as shown in FIGS. 1A and FIG. 3. Therefore, the length of sliding of the seal ring 15 is determined by the annular hermetic space 22 formed at the rear end portion of the outer cylinder 3.

On the other hand, with respect to the notch 20, in order to positively move the O-ring 4 and the O-rings 4', the number of notches 20 in the outer cylinder 3 is equal to the number of projections 18 on the slide cylinder 2, and the notch 20 is provided in at least one portion of the outer cylinder 3. Preferably, notches 20 are provided at two portions, respectively, and for example, if the notches 20 are provided on a diagonal line, that is spaced 180 degrees from each other, the O-ring 4 and O-rings 4' can be pressed uniformly, and can be moved smoothly. More preferably, the notches 20 are provide at least three or more portions, respectively, and when the number of the steps 17 of the outer cylinder 3 is increased so that the number of the O-rings to be mounted thereon can be increased, a larger force is required for pressing the O-rings, and therefore if the number of the portions, at which the O-rings are pressed, is increased, the O-rings can be more effectively moved.

Figure 2B:
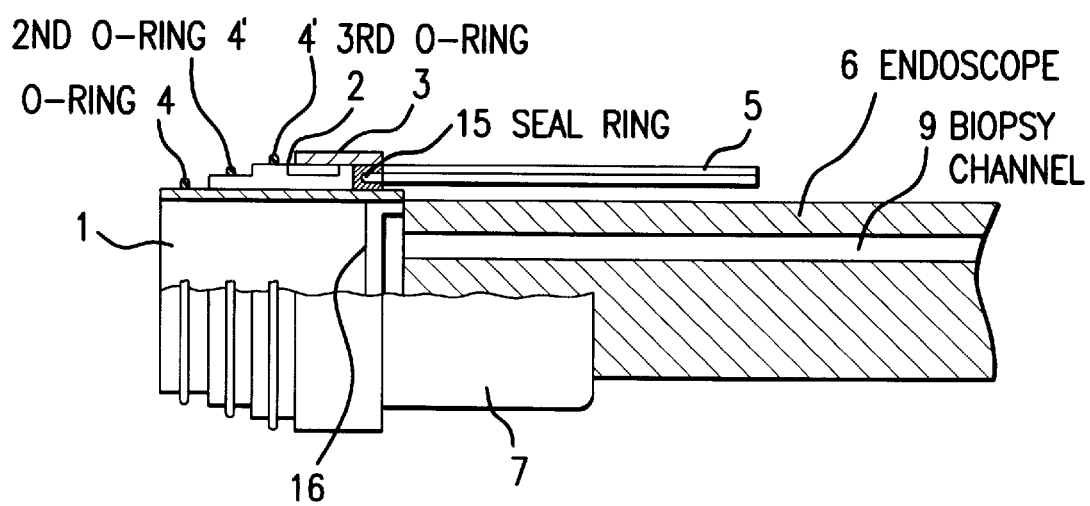
FIG. 2B is a gross-sectional view taken along the line A–A' of FIG. 1A, showing a condition in which an endoscope is attached to the kit of FIG. 1A.
Figure 3:
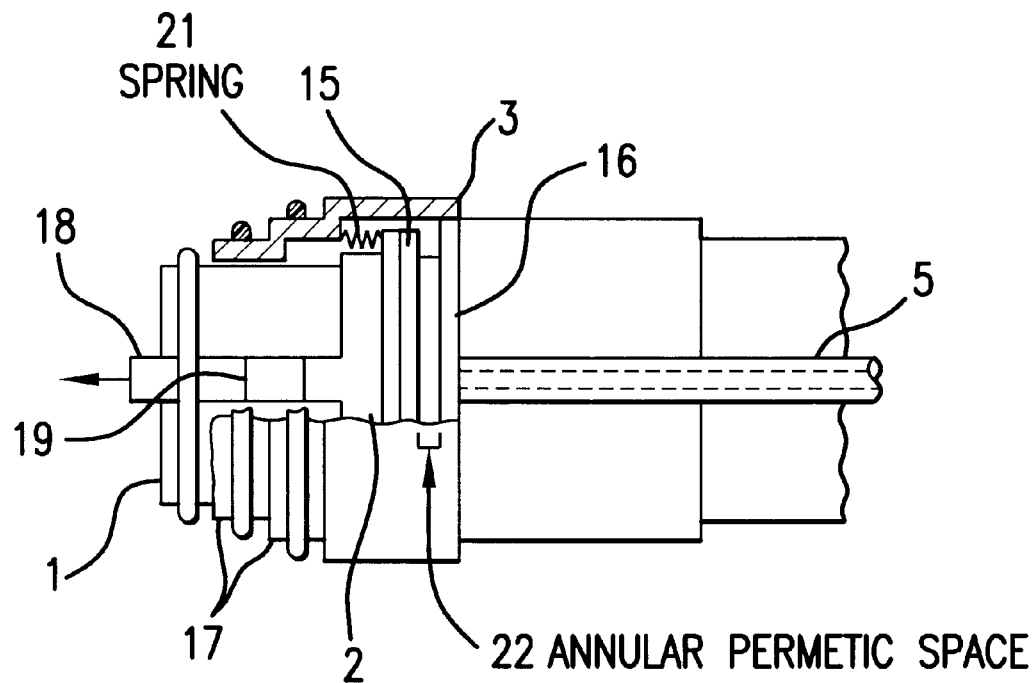
FIG. 3 is cut away view of a the assembled kit including mounted O-rings.

In FIG. 2B, although three O-rings are mounted, the present invention is not limited to this, and the number of the O-rings can be increased, for example, to 4 or 5 by increasing the number of the steps of diminishing outer radii of the outer cylinder 3.

When the ligation kit of the present invention is to be used, the mounting tube 7 is fitted on the distal end of the endoscope 6, and is fixed thereto, and requirements for the mounting tube 7 are that it will both be easily disengaged from the endoscope and that it will not easily leak the air when a varix is drawn under a negative pressure. However, if the fitting of the mounting tube on the endoscope is too tight, this is liable to become the cause of a malfunction of the endoscope, and it is preferred that the mounting tube should be made of a material having an appropriate degree of flexibility and sealing properties. The material is not particularly limited in so far as these conditions are satisfied, and for example, a flexible plastic material and a rubber are particularly suitable.

The material for the common ligating O-rings, used in this kit, is not particularly limited in so far as it has sufficient elasticity to enable the ligation of a varix, and has no problem from the viewpoint of the safety, and for example, natural rubber and isoprene rubber and so on are suitable.

The inner cylinder 1, the outer cylinder 3 and the slide cylinder 2 are required to have a small thickness, a suitable degree of mechanical strength and high dimensional accuracies, and therefore a rigid resin is suitable, and further in order to enhance the operability, they are required to be transparent. The material is not particularly limited in so far as these conditions are satisfied, and examples thereof include polycarbonate resin, a polyvinyl chloride resin, a polysulfone resin, an acrylic resin and an ABS resin.

The seal ring 15, used in the present invention, needs to be made of such a material that keeps the annular hermetic space, and has good sliding properties. In order that the slide cylinder, after projected forwardly, can be returned by drawing the fluid, the slide cylinder and the seal ring must be integrally connected together. If the seal ring is not fixed, there is a disadvantage that the slide cylinder, after being projected, can not be returned, but only the seal ring 15 is returned, and this is not desirable. Therefore, the seal ring 15 needs to be made of a material which can be easily bounded to the slide cylinder, or a material which can be easily bounded to the slide cylinder, or a material which can be easily formed into required dimensional accuracies so that the disengagement of the seal ring can be prevented by the fitting between convex and concave portions. As such, a material, for example, rubber, such as silicone rubber and isoprene rubber, and a flexible plastic material are suitable, but the present invention is not particularly limited to these materials.

The tube, connected to the ligation device, needs to be made of such a material that it is flexible, and will not be twisted and bent when operating the endoscope. As such a material, for example, silicone rubber, flexible vinyl chloride, a polyurethane resin, natural rubber and so on are suitable, but the present invention is not particularly limited to these materials.

In order to clarify the effects of the present invention, a method of using the endoscopic ligation kit of the present invention will now be described. First, the ligation kit of the present invention is attached to a distal end of the endoscope 6, and the tract tube 5 is fixed to the endoscope 6 by a tape or the like. Then, xylocaine jelly or the like is coated to the outer surface of the endoscope, and it is inserted through a mouthpiece fixedly held in the mouth of the patient. Then, the distal end of the ligation kit is held against that part to be ligated in such a manner that this part can be directly viewed as much as possible, and a varix is drawn into the hood by a suction device incorporated in the endoscope. At this time, when it can be confirmed that the drawn varix becomes full in a visual field of the endoscope, the fluid is fed from the syringe to disengage the O-ring, thereby ligating the varix. Then, the fluid is drawn by the syringe 10, thereby returning the slide cylinder 2 to the condition before it is projected, and the next ligation is effected.

With respect to the problem that the conventional kit can not effect the ligations successively in a body cavity, the ligations can be successively effected easily and positively with the use of the endoscope ligation kit of the present invention, and the treatment can be carried out without the use of a guide tube, and the treatment could be effected without damaging the muscosa by the guide tube. Particularly in the event of an emergency involving bleeding, in which every second is important, rapid and positive treatment can be accomplished.

What is claimed:

1. An endoscopic ligation kit for attachment to a distal end of an endoscope so as to draw and ligate tissue in a body cavity comprising:

an inner cylinder;

an outer cylinder having a bore within which the inner cylinder fits which has at least two step portions of diminishing outer radii formed on an outer periphery of a distal end portion of said outer cylinder and having a notch extending from the distal end portion to a maximum outer diameter portion;

a slide cylinder having a bore and having a projection at a distal end portion, the projection conforming in size to the notch in the outer cylinder, and the projection having steps conforming to a shape of the at least two step portions of the outer cylinder, the slide cylinder is received in the outer cylinder in such a manner that the projection of the slide cylinder is fitted in the notch in the outer cylinder and the inner cylinder is fitted in the bore of the slide cylinder;

at least one O-ring mounted on the outer periphery of the distal end portion of the inner cylinder and the at least two step portions of the outer cylinder;

wherein the projection, formed on the slide cylinder, is projected toward the distal end portion, and thereby disengages the at least one O-ring, mounted on the outer periphery of the distal end portion of the inner cylinder, therefrom, and also moves the at least one O-ring, mounted on the at least two step portions of the outer cylinder, to a forwardly-adjacent step of the at least two step portions of the outer cylinder and the outer periphery of the distal end portion of the inner cylinder.

2. The endoscopic ligation kit of claim 1, wherein the inner cylinder further comprises:

a rib disposed at an outer periphery of a rear end portion of the inner cylinder and which integrally connects the outer and inner cylinders.

3. The endoscopic ligation kit of claim 2, further comprising:

an annular hermetic space between the inner cylinder, the outer cylinder and the slide cylinder, wherein a fluid is introduced into said annular space to move the projection of the slide cylinder toward the distal end portion of the outer cylinder.

4. The endoscopic ligation kit of claim 3, further comprising:

a seal ring disposed in the annular hermetic space fixedly secured to a rear end portion of said slide cylinder and slidably connected to said outer cylinder.

5. The endoscopic ligation kit of claim 4, further comprising:

a tract tube connected to the annular hermetic space for communicating fluid the annual hermetic space.

6. The endoscopic ligation kit of claim 5, further comprising:

injection means for injecting the fluid into the annular hermetic space through the tract tube.

7. The endoscopic ligation kit of claim 6, wherein the injection means also removes the fluid from the annular hermetic space and thereby returns the slide cylinder towards the rear end portion of the inner cylinder.

8. The endoscopic ligation kit of claim 1, further comprising a spring arranged in a space in which the slide cylinder can slide, and the slide cylinder, after being pushed toward the distal end portion of the outer cylinder, is returned by the spring.

9. The endoscopic ligation kit of claim 1, further comprising a spring arranged in a space in which the slide cylinder can slide, and the slide cylinder, after being pushed toward a rear end portion of the inner cylinder, is returned by the spring.

10. A method of performing a ligation of an object to be ligated using the endoscopic ligation kit of claim 1, comprising:

attaching the ligation kit to a distal end of an endoscope;

inserting the endoscope through a mouthpiece fixedly held in a mouth of a patient; and ligating the object to be ligated.

* * * * *